United States Patent [19]

McGlave et al.

[11] Patent Number: 5,436,151
[45] Date of Patent: Jul. 25, 1995

[54] METHOD FOR CULTURING HUMAN HEMATOPOIETIC STEM CELLS IN VITRO

[75] Inventors: Philip B. McGlave; Catherine M. Verfaillie, both of St. Paul; Jeffrey S. Miller, Little Canada, all of Minn.

[73] Assignee: Regents of the University of Minnesota, Minneapolis, Minn.

[21] Appl. No.: 862,814

[22] Filed: Apr. 3, 1992

[51] Int. Cl.⁶ .......................... C12N 5/02; C12N 5/08
[52] U.S. Cl. .................. 435/240.1; 435/240.2; 435/240.21; 435/240.241; 435/240.25; 435/284
[58] Field of Search ............... 435/2, 7.24, 240.1, 435/240.2, 240.21, 240.241, 240.243, 240.25, 284

[56] References Cited

U.S. PATENT DOCUMENTS

| | | | |
|---|---|---|---|
| 4,342,828 | 8/1982 | Takaku et al. | 435/41 |
| 4,714,680 | 12/1987 | Civin | 435/240 |
| 4,721,096 | 1/1988 | Naughton et al. | 128/1 |
| 4,808,611 | 2/1989 | Cosman | 514/12 |
| 4,873,191 | 10/1989 | Wagner et al. | 435/172.3 |
| 4,902,783 | 2/1990 | Goda et al. | 530/415 |
| 4,946,437 | 8/1990 | Sredni et al. | 604/49 |
| 4,965,204 | 10/1990 | Civin | 435/240.27 |
| 5,004,681 | 4/1991 | Boyse et al. | 435/2 |
| 5,035,994 | 7/1991 | Civin | 435/2 |
| 5,061,620 | 10/1991 | Tsukamoto et al. | 435/7.21 |
| 5,104,804 | 4/1992 | Humphries et al. | 435/241 |
| 5,139,951 | 8/1992 | Butz et al. | 435/284 |

FOREIGN PATENT DOCUMENTS

| | | |
|---|---|---|
| 341966 | 11/1989 | European Pat. Off. . |
| 395355 | 10/1990 | European Pat. Off. . |
| 455482 | 11/1991 | European Pat. Off. . |
| WO87/06120 | 10/1987 | WIPO . |

OTHER PUBLICATIONS

Verfaillie et al. Blood 82:2045–2053(1993).
Verfaillie et al. Blood 79:2821–2826(1992).
Groenberger in Hematopoiesis (ED. D. W. Golde) pp. 203–242 Churchill Livingstone N.Y. 1984.
H. J. Sutherland et al., *Blood*, 78, 666 (1991).
C. Smith et al., *Blood*, 77, 2122 (May 15, 1991).
M. A. S. Moore, *Blood*, 78, 1 (Jul. 1, 1991).
M. A. S. Moore, *Cancer Supp.*, 2718 (May 15, 1991).
R. M. Schwartz, *PNAS USA*, 88, 6760 (Aug., 1991).
E. F. Srour et al., *Blood Cells*, 17, 287 (1991).
C. C. Fraser et al., *PNAS USA*, 89, 1968 (Mar. 1992).
C. M. Baum et al, *PNAS USA*, 89, 2804 (Apr. 1992).
Costar "Transell" Tech Data Sheet (no date).
H. J. Sutherland et al., *PNAS USA*, 87, 2584 (1990).
J. Brandt et al., *J. Clin. Invest.*, 86, 932 (Sep. 1990).
B. D. Luskey et al., *Annal. N.Y. Acad. Sci.*, 612 398 (1990).
J. Caldwell et al., *J. Cell. Physiol.*, 147, 344 (1991).
L. W. M. M. Terstappen et al., *Blood*, 77, 1218 (Mar. 1991).
R. M. Lemoli et al., *Blood*, 77, 1829 (Apr. 15, 1991).
E. Bruno et al., *Blood*, 77, 2339 (Jun. 1991).
J.-H. Shieh et al., *J. Immunol.*, 147, 2984 (1991).
C. M. Verfaillie et al., *Blood*, 77, 263 (1991).
S. J. Szilvassy, *PNAS USA*, 86, 8798 (1989).
H. J. Sutherland et al., *Blood*, 74, 1563 (1989).
C. Verfaillie et al., *J. Exp. Med.*, 172, 509 (1990).
M. A. S. Moore, *Cancer Surveys*, 9, 7 (1990).
D. M. Bodine, *Ann. N.Y. Acad. Sci.*, 612, 415 (1990).
D. Zipori et al., *Exp. Hematol.*, 8, 816 (1990).

(List continued on next page.)

*Primary Examiner*—David L. Lacey
*Assistant Examiner*—Phillip Gambel
*Attorney, Agent, or Firm*—Schwegman, Lundberg & Woessner

[57] ABSTRACT

A method for culturing mammalian hematopoietic stem cells is provided comprising maintaining a population of human stem cells in fixed, non-contacting relationship to a population of cultured stromal cells, which populations are in liquid stromal growth medium connection, so that the ability of the stem cells to differentiate and self-replicate is maintained during an extended culture period.

13 Claims, 1 Drawing Sheet

OTHER PUBLICATIONS

P. M. Lansdorp et al., *J. Exp. Med.*, 172, 363 (1990).
R. G. Andrews et al., *J. Exp. Med.*, 172, 355 (1990).
H. H. Gerhartz et al., *Blood*, 76, 274a, Abstract 1087 (1990).
W. W. Kwok et al., *PNAS USA*, 83, 4552 (1986).
I. R. Freshney, "Hemopoeitic Cells," in *Culture of Animal Cells*, A. R. Liss, N.Y. (187) at pp. 284–288.
M. Y. Gordon et al., *J. Cell. Physiol.*, 130, 150 (1987).
M. Y. Gordon et al., *Nature*, 326, 403 (1987).
T. Friedmann, *Lancet*, 1271 (Jun. 4, 1988).
G. J. Spangrude et al., *Science*, 241, 58 (1988).
J. Brandt et al., *J. Clin. Invest.*, 82, 1017 (1988).
T. Friedmann, *Science*, 244, 1275 (1989).
I. Bertoncello et al., *Exp. Hematol.*, 17, 171 (1989).
T. M. Dexter et al., *J. Exp. Med.*, 145, 1612 (1977).
S. Gartner et al., *PNAS USA*, 77, 4756 (1980).
I. R. G. Toogood et al., *Leukemia Res.*, 4, 449 (1980).
S. A. Bentley, *Exp. Hematol.*, 9, 308 (1981).
F. T. Slovick et al., *Exp. Hematol.*, 12, 327 (1984).
M. Y. Gordon et al., *Internat. J. Cell Cloning*, 1, 429 (1983).
L. Simonovitch, *J. Cell. Comp. Physiol.*, 64 23 (1964).
T. M. Dexter et al., *J. Cell. Physiol.*, 91, 335 (1977).
R. Shields et al., *J. Cell. Physiol.*, 91 345 (1977).

METHOD FOR CULTURING HUMAN HEMATOPOIETIC STEM CELLS IN VITRO

BACKGROUND OF THE INVENTION

This invention was made with the support of NIH grant number RO1-CA-45814-01. The Government has certain rights in the invention.

The human hematopoietic system is populated by cells of several different lineages. These "blood cells" may appear in bone marrow, the thymus, lymphatic tissue(s) and in peripheral blood. Within any specific lineage, there are a number of maturational stages. In most instances, the more immature developmental stages occur within bone marrow while the more mature and final stages of development occur in peripheral blood.

There are two major lineages: The myeloid lineage which matures into red blood cells, granulocytes, monocytes and megakaryocytes; and the lymphoid lineage which matures into B lymphocytes and T lymphocytes. Within each lineage and between each lineage, antigens are expressed differentially on the surface and in the cytoplasm of the cells in a given lineage. The expression of one or more antigens and/or the intensity of expression can be used to distinguish between maturational stages within a lineage and between lineages.

Assignment of cell to lineage and to a maturational stage within a cell lineage indicates lineage commitment. There are cells, however, which are uncommitted to any lineage (i.e., the "progenitor" cell) and which, therefore, retain the ability to differentiate into each lineage. These undifferentiated, pluripotent progenitor cells will hereinafter be referred to as the "stem cells."

Therefore, all of mammalian hematopoietic cells can, in theory, be derived from a single stem cell. The stem cell is able to self-renew, so as to maintain a continuous source of pluripotent cells. In addition, when subject to particular environments and/or factors, the stem cells may differentiate to yield dedicated progenitor cells, which in turn may serve as the ancestor cells to a limited number of blood cell types. These ancestor cells will go through a number of stages before ultimately yielding a mature cell.

The benefit of obtaining a pure population of stem cells is most readily recognized in the field of gene therapy. Briefly, gene therapy can be used to treat specific diseases caused by a defect in a particular gene. For example, sickle cell anemia is caused by a defect in a single gene. The red blood cells of sickle cell patients contain this defective gene which, in turn, codes for a defective form of the protein hemoglobin. The defective form results in the clinical condition of sickle cell anemia. Sickle cell anemia cannot be "cured" by conventional drug therapies because the underlying defect is in the gene which is included within every cell.

Gene therapy seeks to replace or repopulate the cells of the hematopoietic system with cells that do not contain the defective gene but instead contain a "normal" gene. Using conventional recombinant DNA techniques, a "normal" gene is isolated, placed into a viral vector, and the viral vector is transfected into a cell capable of expressing the product coded for by the gene. The cell then must be introduced into the patient. If the "normal" gene product is produced, the patient is "cured" of the condition. The difficulty is that the transformed cells must be capable of continual regeneration as well as growth and differentiation.

Kwok et al., PNAS USA, 83, 4552 (1986), successfully demonstrated that gene therapy was possible using progenitor cells in dogs. Kwok et al. incorporated certain genes into the equivalent of lineage committed cells by retroviral transfection using standard recombinant DNA techniques and transplanted the transfected cells into the dogs. They obtained expression of the gene product(s) in cells isolated from the dogs. While the cells used by Kwok et al. are capable of growth and differentiation, they are not capable of self-renewal. Thus, any "cure" would be temporary. Stem cells, however, provide a better choice of cells in which to transfect a vector containing a "normal" gene. Stem cells have the capability not only of differentiating into cells of every lineage but also of self-renewal, thus establishing an unlimited supply of such cells. Therefore, by transplanting a stem cell, cells of every type in the hematopoietic system containing the "normal" gene will be continuously provided.

However, stem cells are usually in a resting state, which lowers the efficiency of transfection. Also, one of the most effective methods for viral transfection of hemotopoietic cells known thus far is co-cultivation of the target cells with "high titer, virus-producing cell lines." These virus-producing cell lines are often derived from other species, such as the mouse. Infusion of a human patient with a transfected stem cell population contamination by virus-producing cell lines, especially those derived from another species, is objectionable.

Furthermore, substantial problems have been encountered in (a) identifying the antigenic markers unique to stem cells, (b) isolating homogenous populations comprising substantial numbers of non-lineage committed, pluripotent stem cells and (c) maintaining and, possibly, expanding populations of human stem cells.

Difficulties are also presented by the fact that the stem cell population constitutes only a small percentage of the total number of leukocytes in bone marrow. I. L. Weissman et al. have reported that murine bone marrow cells contain only about 0.02–0.1% pluripotent stem cells. This group reported that Thy-$1^{lo}$Lin$^-$Sca2-$1^-$ murine bone marrow cells are a "virtually pure population of primitive myeloerythroid stem cells." Only 20–30 of these cells were sufficient to rescue one-half of a group of lethally-irradiated mice. See, Stanford University (published European Patent Application No. 341,966), and G. J. Spangrude et al., Science, 241, 58 (1988).

However, at the present time it is not known which antigens are present on stem cells alone or are also present on more differentiated progenitors. As in mice, one marker which has been indicated as present on human stem cells, CD34, is also found on a significant number of lineage committed progenitors. Another antigen which has been reported to provide for some enrichment of progenitor activity is Class II HLA (particularly a conserved DR epitope recognized by a monoclonal antibody designated J1-43). However, these markers are also found on numerous lineage committed hematopoietic cells. The Thy-1 molecule is a highly conserved protein present in the brain and in the hematopoietic system of rat, mouse and man. These species differentially express this antigen and the true function of this molecule is unknown. However, the Thy-1 molecule has been identified on rat and mouse hematopoietic stem cells. This protein is also believed to be present on most human bone marrow cells, but may be absent on stem cells.

Recently, a number of research groups have reported the use of these and other markers to isolate populations of mammalian bone marrow cell populations which are enriched to a greater or lesser extent in pluripotent stem cells. For example, in U.S. Pat. No. 4,714,680, Civin describes a differentiation antigen which is recognized by the monoclonal antibody designated My-10. In normal (i.e., non-leukemic) individuals, this antigen is found on progenitor cells within the hematopoietic system. Accordingly, Civin has described a population of progenitor stem cells which express the antigen recognized by My-10 (i.e., express the CD34 antigen), and has described a method of using My-10 to isolate stem cells for bone marrow transplantation. My-10 has been deposited with the American Type Culture Collection (Rockville, Md.) as HB-8483. My-10 is commercially available from Becton Dickinson Immunocytometry Systems ("BDIS") as anti-HPCA 1. However, using an anti-CD34 monoclonal antibody alone is not sufficient to distinguish between "stem cells," as described by Civin, and the true pluripotent stem cell, since B cells (CD19+) and myeloid cells (CD33+) make up 80-90% of the CD34+ population.

More recently, Becton Dickinson and Company (published European Patent Application No. 455,482) claimed a "substantially pure population of human cells containing pluripotent stem cells that express the CD34 antigen but lack expression of the CD38 antigen and other lineage associated antigens." To isolate this population of human pluripotent stem cells, a combination of anti-CD34 and anti-CD38 monoclonal antibodies are used to select those human progenitor stem cells that are CD34+ and CD38−. One method for the preparation of such a population of progenitor stem cells is to stain the cells with immunofluorescently labelled monoclonal antibodies. The cells then may be sorted by conventional flow cytometry wherein those cells that are CD34+ and those cells that are CD38− are selected for. Upon sorting, a substantially pure population of stem cells is reported to result.

Tsukamoto et al. (U.S. Pat. No. 5,061,620) disclose a method for the negative selection of differentiated and "dedicated" cells from human bone marrow to yield a population comprising "human hematopoietic stem cells with fewer than 5% lineage committed cells." The stem cells are characterized as being "for the most part" CD34+, CD3−, CD7−, CD8−, CD10−, CD14−, CD15−, CD19−, CD20−, CD33−, Class II HLA+ and Thy-1+.

C. Verfaillie et al., $J.$ $Exp.$ $Med.,$ 172, 509 (1990) reported that a two-step purification of low density human bone marrow cells by negative immunomagnetic selection and positive dual-color fluorescence activated cell sorting (FACS) yielded a Lin−CD34+HLA/DR− cell fraction that was 420-fold enriched in pluripotent stem cells capable of initiating long-term bone marrow cultures (LTBMC); over unmanipulated bone marrow mononucleocytes (BMMNC) obtained after Ficoll-Hypaque separation. This group reported that the combination of positive selection for small blast-like cells that are CD34 antigen positive but HLA-DR antigen negative, combined with a more extensive negative selection to deplete the population of CD2, CD19 and CD71, results in an about two- to three-fold greater enrichment in pluripotent stem cells over that previously reported.

The development of cell culture media and conditions that will maintain stem cells in vitro for the extended periods of time required for the procedures involved in gene therapy, identification of growth factors, thorough characterization of cell morphologies and the like, has presented a unique set of obstacles. To date, successful in vitro stem cell cultures have depended on the ability of the laboratory worker to mimic the conditions which are believed to be responsible for maintaining stem cells in vivo.

For example, hematopoiesis occurs within highly dense cellular niches within the bone marrow in the adult and in similar niches within the fetal yolk sac and liver. Within these niches, stem cell differentiation is regulated, in part, through interactions with local mesenchymal cells or stromal cells. Mammalian hematopoiesis has been studied in vitro through the use of various long-term marrow culture systems. T. M. Dexter et al., in $J.$ $Cell$ $Physiol.,$ 91, 335 (1977) described a murine system from which spleen colony-forming units (CFU-S) and granulocyte/macrophage colony forming units (CFU-GM) could be detected for several months, with erythroid and megakaryocytic precursors appearing for a more limited time. Maintenance of these cultures was dependent on the formation of an adherent stromal cell layer composed of endothelial cells, adipocytes, reticular cells, and macrophages. These methods were soon adapted for the study of human bone marrow. Human long-term culture systems were reported to generate assayable hematopoietic progenitor cells for 8 or 9 weeks, and, later, for up to 20 weeks (See, S. Gartner et al., $PNAS$ $USA,$ 77, 4756 (1980); F. T. Slovick et al., $Exp.$ $Hematol.,$ 12, 327 (1984)). Such cultures were also reliant on the preestablishment of a stromal cell layer which must frequently be reinoculated with large, heterogeneous populations of marrow cells. Hematopoietic stem cells have been shown to home and adhere to this adherent cell multi-layer before generating and releasing more committed progenitor cells (M. Y. Gordon et al., $J.$ $Cell.$ $Physiol.,$ 130, 150 (1987)).

Stromal cells are believed to provide not only a physical matrix on which stem cells reside, but also to produce membrane-contact signals and/or hematopoietic growth factors necessary for stem cell proliferation and differentiation. This heterogeneous mixture of cells comprising the adherent cell layer presents an inherently complex system from which the isolation of discrete variables affecting stem cell growth has proven difficult. Furthermore, growth of stem cells on a stromal layer makes it difficult to recover the hematopoietic cells or their progeny efficiently.

Recently, J. Brandt et al., in $J.$ $Clin.$ $Invest.,$ 86, 932 (1990), reported the maintenance of hematopoiesis of CD34+, DR−, CD15−, CD71− human marrow cells in liquid culture for up to 8 weeks, when the culture was supplemented with 48-hourly additions of recombinant IL-1α, IL-3, IL-6 or granulocyte/macrophage colony-stimulating factor (GM-CSF). The establishment of an adherent cell layer was not observed, but cultures containing no exogenous cytokines produced clonogenic cells for only one week. However, even with the optimal cytokine combinations evaluated by Brandt et al., the progenitor cell (blast) population declined throughout the lifetime of these cultures, so that it is not clear that stem cell survival or proliferation is supported by this methodology.

Therefore, a need exists for methods for the long-term in vitro culture of human stem cells.

SUMMARY OF THE INVENTION

The present invention provides a method for the long-term culture of mammalian, preferably murine or human, stem cells. The present method comprises maintaining a population of stem cells in a fixed, non-contacting relationship to a population of cultured stromal cells, which populations are in liquid stromal cell growth medium connection during culturing. Preferably, the populations are both human and allogeneic, most preferably they are autologous, although they need not be. For example, the stromal cell population and the stem cell population are preferably adhered to, or supported by, separable cell culture substrata, which substrata are immersed in a stationary or flowing body of stromal cell culture medium. Thus, the present method at least substantially conserves the stem cell population throughout the culturing period, while preserving, and preferably enhancing, its ability to differentiate into lineage-committed progenitor cells (hereinafter referred to as "committed progenitors"). As used herein, the term "stromal cells" includes (1) human allogeneic or autologous stromal cells, or non-human stromal cells,
(2) human or non-human stromal cell lines, and
(3) human or non-human virally infected cell lines, such as immortalized embryonic fibroblasts which are effective to provide "feeder layers" for stem cell populations.

The present method also greatly facilitates the characterization and isolation of cultured human stem cells, or of more various cell populations containing said stem cells but not containing a stromal cell "feeder layer," since the method does not require direct contact between the stromal cell layer and the stem cells. Furthermore, while prior culture methods for stem cells which do not employ contact layers of stromal cells can only maintain viable stem cells for about 2-3 weeks in the absence of added cytokines, the present method can maintain viable populations of normal human stem cells for at least 5 weeks in the absence of added cytokines. Preferably, the present system can be maintained for up to six months or more.

Although the absolute number of stem cells declines over time, the number of stem cells remaining at five weeks is greater than that obtained using prior art methods in which hematopoietic cells are grown in direct contact with stroma or than that described when hematopoietic cells are grown in cytokine-augmented media not containing stromal cells. For example, in accord with the present method, about 40–50% of the initial stem cell population can be preserved after 5 weeks. Thus, the present invention is also advantageous in that it does not require the addition of exogenous cytokines to the stromal cell culture medium, such as those disclosed by J. Brandt et al., discussed above, but can employ relatively simple growth media, such as the complete medium described in the working examples below.

The present invention also comprises a population of self-replicating stem cells prepared in accord with the present method, e.g., free of a stromal cell feeder layer, which are preferably Lin−CD34+DR−. Unexpectedly, it was also found that the number of committed progenitors increases markedly during the culture period. Although not intending to be bound by any theory of action, it is believed that this effect may be due to removal of the population of stem cells from direct contact with the stromal cells which, in turn, may lift the negative regulation of the stem cell population which is necessarily operative in vivo. The invention also provides an improved method for expanding the population of committed progenitors over that present in the initially cultured population, while maintaining or conserving a population of self-replicating, pluripotent stem cells.

DETAILED DESCRIPTION OF THE INVENTION

Figure 1:
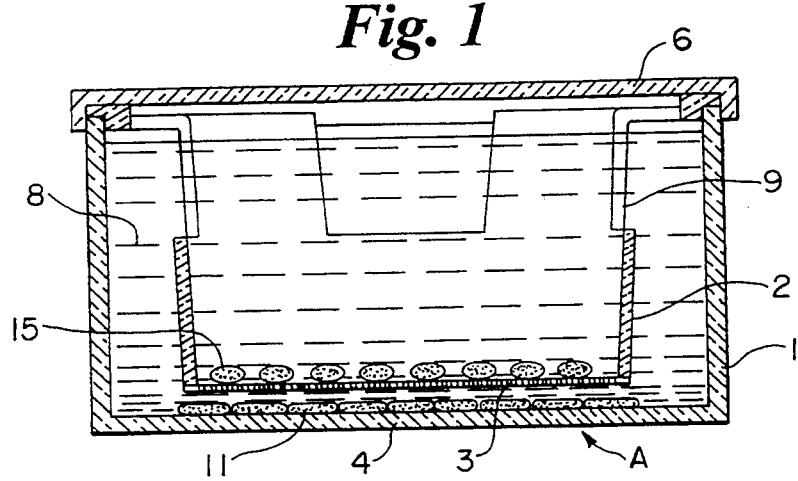
FIG. 1 is a schematic cross-sectional view of a cell culture chamber useful in the present method.

Preferably, the stem cell population is derived from mammalian bone marrow, as from human bone marrow, e.g., by centrifugation and the immunomagnetic and FACS procedures as described in C. Verfaillie et al., *J. Exp. Med.*, 172, 509 (1990) (hereinafter "C. Verfaillie et al."), which yields cell populations highly-enriched in human stem cells which are characterized by being Lin−CD34+DR−. Allogeneic mammalian stromal cells can be obtained as described by T. M. Dexter et al., *J. Exp. Med.*, 145, 1612 (1977), and are preferably irradiated and subcultured on the present substrata (e.g., in plastic cell culture wells) as described in C. Verfaillie et al., or as by J. Caldwell et al., *J. Cell. Phys.*, 147, 344 (1991).

Preferably, the stem cell population is supported by a microporous membrane which maintains the stem cells and any associated cells in liquid medium contact with the stromal cell population. Preferably, the membrane separates the two populations, e.g., by about 0.25–2.0 mm, as in the Examples. The pores of the membrane can vary in size, so long as they allow culture medium and its components to contact the stem cells, while avoiding stromal cell contact and providing adequate support for the stem cells. Preferably, the microporous membrane is formed of a synthetic polymer, which can be coated with a cell-adherence promoting peptide, such as mammalian (human) collagen, laminin, fibronectin or the subunits thereof possessing the ability to promote hematopoietic cell attachment. For example, such peptides are disclosed in U.S. Pat. Nos. 5,019,546, and 5,059,425. The stem cells may also be attached to the interior of a microporous tube or hollow fiber, while the stem cells are maintained in a fixed relationship from the exterior of the tubing, e.g., on the walls of a chamber containing the growth medium.

During the practice of the present method, the liquid growth medium may be held as a stationary body which envelops both populations of cells, and is preferably about 25–100% exchanged at fixed intervals, e.g., of 8 hrs–14 days, preferably of about 1–10 days. Such regular exchanges of stromal cell growth medium have been reported to enhance the production of endogenous growth factors, such as granulocyte/macrophage colony stimulating factor (GM-CSF), from stromal cells, by J. Caldwell et al., *J. Cellular Phys.*, 147, 344 (1991).

Alternatively, the culture medium can be continuously circulated through a culture chamber that contains the stem cells and the stromal cells, and replaced/replenished at a site remote from the culture chamber, or the stem cells and the stromal cells can be cultured in separate culture chambers, so long as they remain in stromal cell culture medium liquid connection.

One commercially-available device that contains separable cell culture substrata for both the stromal cell population and the stem cell population is the Transwell™ series of cell culture chambers available from Costar Corp., Cambridge, Mass., USA. As depicted in schematic cross-section in FIG. 1, each Transwell® chamber (A) comprises a flat-bottomed plastic lower compartment 1, and a plastic upper compartment 2, which can be removably inserted into compartment 1, so that the collagen-coated, microporous membrane 3 (0.45 μm pore diameter), which forms the bottom of compartment 2, is held in a fixed, essentially parallel relationship to the inner surface of the bottom (4) of the compartment. This assembly is covered by a removable lid 6. In use, stroma cells 11 are added to the bottom of lower compartment 1, and a preselected amount of liquid culture medium 8 is added. Stem cells 15 are added to the upper surface of microporous membrane 3 and the upper compartment (or transwell) 2 is inserted into the lower compartment. Opening 9 in the sidewall of the transwell 2 permits addition of or removal of the medium 8 from the exterior void space of the chamber A. The cover 6 is then replaced. Following the culture period, which can be as long as 3–6 months, the cover 6 is removed; the transwell is removed, and all or a portion of the stem cells 15 are then removed from the microporous membrane and employed in the end use.

For example, the stem cells may be used in bone marrow transplantation to repopulate the bone marrow of a patient whose "defective" marrow has been destroyed by means such as lethal irradiation, chemotherapy, or other agents causing aplasia without recovery. For example, the ability to cultivate large numbers of committed progenitors from stem cells to be used for transfusion therapy may be particularly useful in circumstances where it can be foreseen that a patient will require blood products support, such as when there are impending plans to administer high-dose chemotherapy or in the case of autologous bone marrow transplantation following lethal irradiation. Under these circumstances, it may be useful to cultivate and store the patient's own (autologous) population of committed progenitors before initiating chemotherapy in order to avoid the need for transfusion of blood products obtained from allogeneic donors. Culture of autologous stem cells in the Transwell system or variants of this system allows the cultivation of a population of committed progenitors which, when transfused into the recipient, can be expected to have the following attributes:

1) Committed progenitors, unlike granulocytes and platelets currently used for transfusion, can be frozen and stored indefinitely. These features are particularly important in the case of granulocyte support since granulocytes from allogeneic donors are difficult to obtain, cannot be frozen, have a stored shelf life of less than 24 hours, and have a half-life of less than five minutes after transfusion into an allogeneic recipient.
2) The committed progenitors derived from cultured stem cells provide a sustained and long-lasting population of red blood cells, granulocytes and/or platelet precursors which mature in vivo after transfusion and can be expected to have a considerably longer half-life than mature blood products obtained from normal donors.
3) The cultivation of committed progenitor populations from autologous stem cells in accord with the present method, prior to an anticipated need for transfusion, obviates the need to locate, type (cross match) and phlebotomize normal, volunteer blood donors.
4) Use of cultivated, autologous committed progenitors also obviates the need for extensive ABO typing and safety monitoring, the risk of donor/recipient transfusion reactions, the risk of infection with HIV, CMV, hepatitis viruses and other blood-borne infections associated with current donor/recipient blood product transfusion methods.
5) This approach will also provide adequate blood support in the case of individuals with rare ABO blood types for whom suitably matched donors cannot be located in a timely fashion or at all.
6) Cultivation of autologous committed progenitors will also eliminate the problems of recipient "sensitization" to allogeneic blood products commonly seen in patients receiving multiple transfusions.
7) Use of committed progenitors will also reduce the frequency of blood transfusions compared to use of allogeneic, mature blood products since committed progenitors cultivated in accord with the present invention can be expected to have a considerably longer half-life than blood components obtained from normal allogeneic donors, as discussed above.

Although it is currently envisioned that the present method would be primarily used for cultivation of autologous committed progenitors or mature blood cells prior to an anticipated need for blood component support, it is also believed that the present method can be used to cultivate a committed progenitor population suitable for transfusion from normal donors to allogeneic recipients. Thus, stem cells from normal donors known to be free of infection could be cultivated to produce large quantities of committed progenitors or mature blood cells. The committed progenitors are suitable for long-term storage and subsequent transfusion into allogeneic recipients. This may be particularly useful when stem cells from donors of known rare blood types are cultivated and stored. Therefore, the present method may lead to the elimination of the current cumbersome, expensive and sometimes dangerous practices involved in transfusion mature blood components from human donors.

The stem cells may also be used in gene therapy wherein a gene producing a protein, enzyme or other product is inserted into the DNA of the stem cells which are then transplanted into a patient's bone marrow. See, for example, B. P. Luskey et al., *Annals. N.Y. Acad. Sci.*, 612, 398 (1990) and B. A. Naughton et al. (U.S. Pat. No. 4,721,096).

To effect gene therapy with a substantially pure population of human stem cells, the following general method may be used to insert a gene into these progenitor cells. For a review of the methodologies that are applicable, see Friedman, *Science*, 244, 1275 (1989) and *Lancet*, Jun. 4, 1988, p. 1271.

In order to introduce a normal gene, a normal gene is first isolated from the cells of a donor. The cells may be isolated from tissue(s), blood or other body fluids, including bone marrow. To find a gene coding for the defective protein, DNA from the donor cells is isolated and cleaved by enzymatic digestion into segments of varying length by means known to those skilled in the art. The segments of DNA then may be inserted individually into vectors containing the appropriate regulatory sequences for expression of a gene product. The vectors then can be screened by conventional means such as Northern blotting if the sequence for the normal gene is known or the expression product can be screened by Western blotting.

Alternatively, if the DNA sequence of the desired gene or the sequence of the normal protein is known, the gene can be made by synthetic chemistries such as on a DNA synthesizer (Applied Biosystems). In any case, the method of isolation or construction of the gene sequence can yield a "normal" gene that codes for the desired gene product.

Once the DNA containing the gene is prepared, the DNA can be inserted into the population of stem cells isolated as above. The DNA can be inserted by 1) physical methods such as coprecipitation with calcium phosphate, electroporation or microinjection (e.g., U.S. Pat. No. 4,873,191), and/or by 2) the use of viral vectors such as adenoviruses, if the DNA is less than approximately 7-8 kB, or retroviruses for longer segments of DNA. In the latter case, the DNA of the retrovirus is cut with a restriction enzyme and the human DNA containing the desired sequence is inserted and ligated. The retrovirus containing the insertion then is transfected into the stem cells. The stem cells then can be assayed for production of the desired protein. See, e.g., U.S. Pat. No. 4,902,783.

In general, molecular DNA cloning methods are well known in the art and are not limiting in the practice of this invention. For a further description of similar methods, see Friedmann, *Science*, 244, 1275 (1989) and *Molecular Cloning: A Laboratory Manual* (2nd ed.), Cold Spring Harbor Laboratory Press, Sambrook, Fritsch and Maniatis eds. (1989).

To transplant the stem cells containing the desired gene, the cells may be introduced into the bone marrow of the patient by conventional means of bone marrow transfer. Typically, this involves the delivery of the cells by intravenous infusion over a period of time. The bone marrow of the patient may be lethally irradiated prior to infusion to assure that the transplanted stem cells fully replace the existing bone marrow cells.

The present method of culturing stem cell populations can facilitate gene therapy in a number of ways:

1) Stem cells are usually in a resting state. Gene insertion (transfection) is performed more efficiently when cells are in cycle. Culture of the stem cell population in accord with the present method stimulates cycling of the stem cells and can be expected to increase the efficiency of transfection.

2) Growth of stem cells on a stromal layer makes it difficult to recover the hematopoietic stem cells or their progeny efficiently. Cultivation of stem cells via the present method allows complete and efficient recovery of the stem cell population and its progeny simply by removal of the supported stem cells from the system.

3) Currently, one of the most efficient methods for transfection of cells is co-cultivation of the target cells with "high titer, virus-producing cell lines." These virus-producing cell lines are often derived from other species such as the mouse. Patient infusion with a transfected stem cell population contaminated by virus-producing cell lines, especially those from another species, is objectionable. The present method allows recover of stem cells and their progeny which have been exposed to the high titer virus-producing cell line without contamination of the stem cell population by these foreign cell lines.

The invention will be further described by reference to the following detailed examples, wherein human bone marrow was obtained from 22 healthy young volunteers after informed consent by aspiration from the posterior iliac crest in preservative free heparin. Bone marrow mononuclear cells (BMMNC) were obtained after Ficoll-Hypaque separation (Sigma Diagnostics, St. Louis, Mo.) (s.g. 1.077).

Bone marrow mononuclear cells (BMMNC) were purified further in an initial counterflow elutriation step, by suspending BMMNC in PBS supplemented with 0.3% BSA (Sigma) and 0.01% EDTA (Sigma). The cells were injected into an elutriator system with standard separation chamber (Beckman Instruments, Inc., Palo Alto, Calif.) primed with Iscove's Modified Dulbecco's Medium (IMDM), 5% fetal calf serum (FCS) and 0.01% EDTA. Rotor speed and temperature were maintained at 1,950 RPM and 10° C. After loading, 200 ml of effluent was collected at a flow rate of 14 ml/min. The rotor was then stopped and the remaining BMMNC flushed from the separation chamber. Cells collected in fraction 14 were then depleted from T-lymphocytes and NK cells by sheep erythrocyte rosetting as described by C. M. Verfaillie et al., *Blood*, 77, 263 (1991). Further depletion of committed lymphold and myeloid/monocytic cells was obtained by negative immunomagnetic depletion of cells expressing CD2, CD3, CD11b, CD19, CD56, CD71, MY8 and glycophorin-A antigens using the methods described in C. Verfaillie et al.

The resultant lineage negative (Lin−) cells were labeled with anti-CD34 and anti-HLA-DR antibodies as described by C. Verfaillie et al. Cells were sorted on a FACS-Star-Plus laser flow cytometry system (Becton-Dickinson, Mountain View, Calif.) equipped with a Consort 40 computer. Cells were initially selected for low vertical and very low/low horizontal light scatter properties. Cells selected in the first window expressing high numbers of CD34 antigens and lacking HLA-DR antigen expression were then sorted to yield DR− cells, as described by C. Verfaillie, et al. These DR− cells correspond to the highly stem cell-enriched population designated as Lin− 34+DR− in C. Verfaillie et al. The latter windows were chosen on the basis of the fluorescence pattern of control samples labeled with mouse IgG1-PE and mouse IgG2a-FITC antibodies.

Example 1. In Vitro Culture of DR− Stem Cells

The DR− cells were cultured as follows:
1. "Stroma-Free" cultures: $2-8 \times 10^3$/ml DR− cells were plated in complete media in wells of 24 (1 ml) or 6 well plates (4 ml) (Costar, Cambridge, Mass.). No stromal layers were established. No cytokines were added to the complete media. The culture media consisted of IMDM with 12.5% fetal calf serum (HyClone Laboratories, Logan, Utah), 12.5% horse serum (HyClone Laboratories), 2 mM L-glutamine (Gibco Laboratories), penicillin 1,000 U/m and streptomycin 100 U/ml (Gibco) and $10^{-6}$M hydrocortisone (A-Hydrocort) (Abbott Laboratories, North Chicago, Ill.).

2. "Stroma-contact" cultures: Irradiated stromal cells were subcultured in 6 well ($2 \times 10^6$ cells suspended in 4 ml) or 24 well ($0.5 \times 10^6$ cells suspended in 1 ml) plates. DR⁻ cells ($2-8 \times 10^3$/ml) were then plated onto the irradiated allogeneic stromal layers as described C. Verfaillie et al. (FIG. 1B).

3. "Stroma-non-contact" cultures: Transwell ™ cultures consisted of allogeneic irradiated stromal cells derived from the same donors as the stromal cells used in the "stroma-contact" cultures subcultured in the bottom well of 6 ($2 \times 10^6$ cells suspended in 3 ml) or 24 ($0.5 \times 10^6$ cells suspended in 0.8 ml) well Transwell ™ plates. A collagen treated transwell insert (0.45 μm microporous filter) (Costar) was then placed on top of the stromal layer, and sorted DR⁻ cells plated in the upper wells ($2-8 \times 10^3$ cells in 0.2 ml complete media for 24 well plates, or $4-32 \times 10^3$ DR⁻ cells in 1 ml complete media for 6 well plates).

4. Maintenance of cultures: All cultures were maintained in a humidified atmosphere at 37° C. and 5% $CO_2$. At weekly intervals "stroma-contact" and "stroma-free" cultures were fed by removing half of the cell-free supernatant and replacing it with fresh complete media. For "stroma-non-contact" cultures, half the media from the bottom wells only was removed and replaced by fresh complete media.

5. Evaluation of long-term cultures: Non-adherent and adherent cells recovered from selected "stroma-contact" cultures after treatment with 0.15% collagenase (Boehringer Manheim) were assayed at different time points in the short term methylcellulose assay for the presence of committed progenitors. In the short-term methylcellulose assay, the DR⁻ cells were plated in clonogenic methylcellulose assay supplemented with 3 IU recombinant erythropoietin (Epoetin) (Amgen, Thousand Oaks, Calif.) and 10% conditioned media from the bladder carcinoma cell line 5637 as described by C. Verfaillie et al. Cultures were incubated in a humidified atmosphere at 37° C. and 5% $CO_2$ for 18-21 days. The cultures were assessed at day 18-21 of culture for the presence of CFU-MIX, granulocyte/macrophage colony forming units (CFU-GM) and erythroid burst-forming units (BFU-E) as described in the C. Verfaillie et al.

Likewise, cells from selected "stroma-free" cultures or present in the upper wells of selected "stroma-non-contact" cultures were collected at different time points, enumerated under a hemocytometer, examined for their morphology and phenotype and assayed for the presence of committed or primitive progenitors. To determine phenotype, cells collected from the upper wells of transwell cultures were analyzed at week 5 of culture for the presence of CD34+/HLA-DR+ and CD34+/HLA-DR⁻ cells. Cells were labeled with anti-CD34-PE antibody (Becton-Dickinson) and anti-HLA-DR-FITC antibody (Becton-Dickinson). Cells were analyzed for the expression of these antigens on a FACS-Star-Plus flow cytometry system, equipped with a Consort computer. PE and FITC coupled isotype-matched mouse immunoglobulins were used as controls.

To carry out limiting dilution assays (LDA), at day zero DR⁻ cells (24 replicates per concentration) (experiment 1-3: 1000, 333, 111 or 33; experiment 4: 500, 200, 100 or 20; experiment 5-6: 400, 150, 50, 15 DR⁻ cells/well) were plated onto $3 \times 10^4$ irradiated allogeneic stromal cells, subcultured in 96 well plates (Costar) (day-0 limiting-dilution assay=LDA). See H. J. Sutherland, et al., *Blood,* 78, 666 (1991) and *PNAS USA,* 87, 2584 (1990). Likewise, cells recovered after 5 weeks from collagenase treated "stroma-contact" cultures or transwell-inserts of "stroma-non-contact" cultures initiated at day 0 with 35,488 (experiments 1-3), 19,680 (experiments 4-6) or 14,760 (experiments 5-6) DR⁻ cells were plated in LDA (cell number=the equivalent of 1,000, 333, 111 and 33 (experiments 1-3), 500, 200, 100, or 20 (experiment 4) or 400, 150, 50, 15 (experiments 5-6) DR⁻ cells at day 0; 23 ±1 replicates per concentration). Stromal layers used to perform LDA at day 0 and at day 35 after initial culture in "stroma-contact" or "stroma-non-contact" cultures were derived from bone marrow samples from the same allogeneic donor. Cultures were maintained in a humidified atmosphere, at 37° C. and 5% $CO_2$ and fed weekly with 75 μl fresh media. At week 5, non-adherent and adherent cells were collected as described in C. Verfaillie, et al. and evaluated for the presence of committed progenitors. The absolute number of LTBMC-IC present in the different cell populations was calculated as the reciprocal of the concentration of test cells that gave 37% negative cultures using the Poisson statistics (E. H. Porter et al., *J. Cancer,* 17, 583 (1963)) and the weighted mean method (C. Taswell, *J. Immunol.,* 126, 1614 (1981)).

Results of experimental points obtained from multiple experiments were reported as the mean ±1 standard error of the mean (SEM). Significance levels were determined by two-sided students t-test analysis.

DR⁻ cells were suspended in fetal calf serum, horse serum and hydrocortisone containing media but without exogenous cytokines. Cell suspensions were plated either without stromal layer ("stroma-free"), directly onto allogeneic irradiated stromal layers ("stroma-contact") or in transwells-inserts which separated DR⁻ cells from the stroma by a 0.45 μm microporous collagen-coated membrane allowing free passage of diffusible factors but preventing cell-cell contact ("stroma-non-contact") as shown in FIG. 1. These translucent transwell inserts were placed one mm above the stromal layer which was adherent to the bottom well but remained completely separated from the transwell inserts throughout the culture period. Repeated visual inspection demonstrated that no adherent stromal layer was formed in "stroma-free" cultures nor in the transwell inserts of "stroma-non-contact" cultures.

Figure 2:
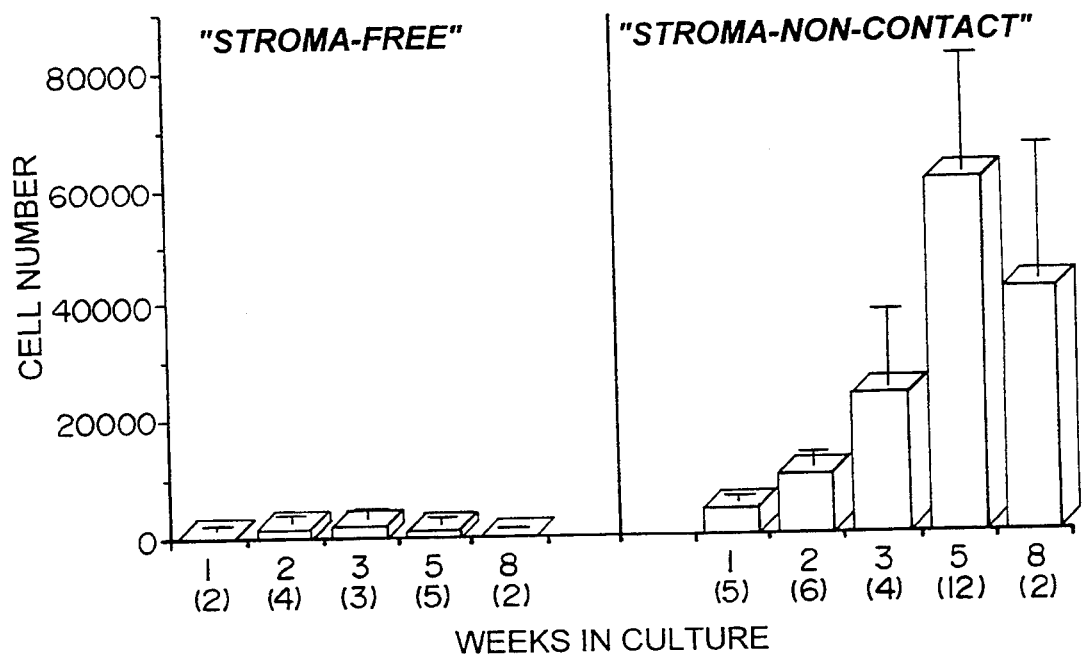
FIG. 2 is a graphical depiction of the extent of proliferation of DR− stem cells in "stroma free" and "stroma-non-contact" cultures. The data represent the mean ±SEM cell number present in cultures initiated with 5,000 DR− cells. (x)Number between brackets on the X-axis represent the number of experiments.

When DR⁻ cells were plated in the absence of a stromal layer ("stroma-free"), a progressive decline in cell number is observed (FIG. 2). Virtually all cells were monocytes at week 2. In contrast, serial evaluation of "stroma-non-contact" cultures revealed that, after an initial decline in cell number at week 1, the cell number in the transwell-inserts increased steadily (FIG. 2). At week 1, more than 55% of cells were blasts admixed with promyelocytes. Over the next 4 weeks, the percentage of blasts declined; the percentage of promyelocytes remained constant and a gradual increase in mature myeloid elements was seen. At week 8, blasts and myeloid precursors decreased further with a reciprocal increase in monocytes. FACS analysis of cells present in "stroma-non-contact" cultures at week 5 demonstrated that 4.1 ±1.2% of cells were CD34+/HLA-DR+ (n=6) associated with more differentiated hematopoietic progenitors, and 1.1 ±0.16% of cells remained CD34+/HLA-DR− (n=6). Taking into account that the total cell number was 8 ±3.8 fold higher at week 5 compared with day 0, these studies demonstrate that for each DR− cell used to initiate the cultures 19 ±5 CD34+/HLA-DR+ cells were generated and approximately 6% of DR− cells could be conserved for a minimum of 5 weeks.

These experiments demonstrate that, although stroma is important for in vitro hematopoiesis, direct contact between stem cells and the stromal layer is necessary neither for the differentiation of such progenitors into more differentiated 34+/DR+ cells and mature myeloid cells, nor for the conservation of a fraction of primitive 34+/DR− progenitors.

To test this hypothesis further, cells recovered from "stroma-free," "stroma-contact" and "stroma-non-contact" were plated in cultures in the methylcellulose progenitor assay to evaluate the production of clonogenic cells. As demonstrated by the data summarized in Table 1, very few clonogenic cells were present in "stroma-free" cultures during the first 3 weeks, while none were present in such cultures at weeks 5 and 8.

"stroma-contact" cultures (Table 1). This indicates that in contrast to differentiation-inducing factors, negative regulators of stem cells are either not released or reach the cultured stem cells in lower concentrations in "stroma-non-contact" cultures. Alternatively, direct hematopoietic cell-stroma interaction may actually be required to convey differentiation-inhibiting signals.

Example 2. Self-Renewal of Stem Cell Populations

D. Zipori et al., *Exp. Hematol.*, 6, 816 (1980) have postulated that one of the major roles of stromal tissue may be to maintain the most primitive progenitor ("stem cell") compartment. Removal of the close cell-cell interactions between hematopoietic and stromal cells could, therefore, induce differentiation only and result in an accelerated exhaustion of the stem cell pool (L. Siminovich et al., *J. Cell. Comp. Physiol.*, 64, 23 (1964)). In order to test this possibility, 6 separate experiments were conducted to compare the absolute number of stem cells capable of initiating long-term bone marrow cultures (LTBMC-IC) still present after culture of DR− cells for 5 weeks in "stroma-contact" or "stroma-

TABLE 1

Recovery of committed progenitors from primitive DR− cells culture in "stroma-free," "stroma-contact" and "stroma-non-contact" cultures.

| CULTURE | WEEK (n =) | NO. OF COLONIES PER 5,000 DR− CELLS[a] | | |
|---|---|---|---|---|
| | | CFC | CFU-GM | BFU-E |
| Sorted DR− cells | 0(5) | 66.4 ± 13.9 | 25.5 ± 1.65 | 40.9 ± 12.6 |
| "Stroma-free" | 1(3) | 12.2 ± 5.1 | 8.8 ± 1.8 | 3.3 ± 3.3 |
| | 2(4) | 4.2 ± 3.2 | 1.8 ± 1.2 | 2.5 ± 2.5 |
| | 3(2) | 13.3 ± 0 | 13.3 ± 0 | 0 ± 0 |
| | 5(4) | 0 ± 0 | 0 ± 0 | 0 ± 0 |
| | 8(2) | 0 ± 0 | 0 ± 0 | 0 ± 0 |
| "Stroma-contact" | 1(4) | 81.7 ± 10 | 39.3 ± 8.1 | 45.3 ± 9.9 |
| | 2(5) | 85.8 ± 17.7 | 53.7 ± 12.1 | 35.7 ± 7.7 |
| | 3(2) | 96.3 ± 23.3 | 58.3 ± 15 | 38.3 ± 8.3 |
| | 5(12) | 150 ± 16.7 | 108 ± 23 | 44.1 ± 9.8 |
| | 8(2) | 47.8 ± 1.8 | 34.95 ± 1.65 | 13.3 ± 3.3 |
| "Stroma-non-contact" | 1(4) | 107.5 ± 15* | 88.8 ± 8.8* | 25.4 ± 4.2 |
| | 2(5) | 126.8 ± 30* | 86.4 ± 28.8* | 31.8 ± 9.7 |
| | 3(2) | 165.7 ± 79 | 154 ± 74 | 9.5 ± 2.5 |
| | 5(12) | 333 ± 41 * | 273 ± 37 * | 28.3 ± 9.8* |
| | 8(2) | 99.6 ± 19.6* | 98 ± 18 * | 1.6 ± 1.6 |

[a]Colonies were enumerated at day 14–19 (CFC = colony forming cells; CFU-GM = granulocyte-macrophage colony-forming-unit; BFU-E = erythroid burst-forming-unit). Results are the mean number ± SEM of colonies obtained from 5,000 DR− cells. (x): Values between brackets represent the number of experiments. Students t-test: *p ≤ 0.01: Comparison between "stroma-free" and "stroma-non-contact" cultures.
: p ≤ 0.1: Comparison between "stroma-contact" and "stroma-non-contact" cultures.

"Stroma-contact" cultures yielded an increasing number of clonogenic cells over the first 5 weeks with a decrease in committed progenitor recovery by week 8. When DR− cells were plated in "stroma-non-contact" culture, a similar increase was observed in the generation of committed progenitors during the first 5 weeks, which declined by week 8. These studies demonstrated that bone marrow derived stromal cells are required for the proliferation and differentiation of primitive hematopoietic progenitors when no exogenous cytokines are provided. However, induction of differentiation does not require direct contact between the hematopoietic progenitors and the stromal layer, suggesting that diffusible factors are released from the stromal environment that induce differentiation of primitive progenitors placed in a transwell-insert 1 mm above the stromal layer.

"Stroma-non-contact" cultures also differed from "stroma-contact" cultures in that a significantly greater number of CFU-GM were recovered from "stroma-non-contact" cultures at weeks 5 and 8 compared with non-contact" cultures with the absolute number of LTBMC-IC present in the FACS sorted DR− population. The results of these experiments are summarized in Table 2, below.

TABLE 2

Stem cells are conserved equally well when primitive DR- cells are cultured in "stroma-contact" and "stroma-non-contact" cultures.

| | ABSOLUTE NUMBER OF LTBMC-IC SORTED DR− CELLS[a] | | |
|---|---|---|---|
| Experiment | Sorted DR− cells | "Stroma-contact" | "Stroma-non-contact" |
| 1 | 1/73 | 1/415 | 1/180 |
| 2 | 1/204 | 1/825 | 1/251 |
| 3 | 1/132 | 1/480 | 1/283 |
| 4 | 1/102 | 1/303 | 1/168 |
| 5 | 1/68 | 1/600 | 1/208 |
| 6 | 1/168 | — | 1/349 |

TABLE 2-continued

Stem cells are conserved equally well when primitive DR- cells are cultured in "stroma-contact" and "stroma-non-contact" cultures.

ABSOLUTE NUMBER OF LTBMC-IC SORTED DR− CELLS[a]

| Experiment | Sorted DR− cells | "Stroma-contact" | "Stroma-non-contact" |
|---|---|---|---|
| Mean ± SEM | 1/123 ± 22* | 1/524 ± 89 | 1/239 ± 28 |

[a]The absolute number of LTBMC-IC present in the different cell populations was calculated as the reciprocal of the concentration of test cells that gave 37% negative cultures using the Poisson statistics and the weighted mean method.
*p = 0.001 and p = 0.009: Comparison between day 0 LDA and "stroma-contact" and "stroma-non-contact" cultures respectively.
: p = 0.009: Comparison between "stroma-contact" and "stroma-non-contact" cultures.

As shown by the data summarized on Table 2, one LTBMC-IC per 123 ±22 sorted DR− cells was present at day 0. When DR− cells were cultured for 5 weeks in either "stroma-contact" culture (1 LTBMC-IC per 524 ±89 initially sorted DR− cells; p=0.001) or "stroma-non-contact" culture (1 LTBMC-IC per 239 ±28 initially sorted DR− cells; p=0.009) and then assessed for their stem cell content, a decrease in absolute number of LTBMC-IC was observed. (Table 2.) However, the decrease in stem cells capable of initiating long-term in vitro hematopoiesis was significantly greater in "stroma-contact" than in "stroma-non-contact" cultures (p=0.009). Thus, the present method eliminates the need to provide direct hematopoietic cell-stroma contact to maintain a fraction of pluripotent stem cells which are capable of initiating in vitro hematopoiesis. Surprisingly, culture of normal stem cells separated from the adherent stromal layer results in an increased generation of committed granulocyte-macrophage progenitors and conserves stem cells with long-term in vitro repopulating capacity better than culture of stem cells in direct contact with the stromal layer.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A cell culture method comprising culturing in vitro a population of hematopoietic human stem cells supported in a non-contacting relationship to a supported population of cultured stromal cells, which populations are in a body of liquid stromal cell growth medium wherein the growth medium does not contain exogenous cytokines, so that the ability of the stem cell population to self-replicate and to differentiate into granulocyte-macrophage progenitors and long-term bone marrow culture initiating cells is maintained.

2. The method of claim 1 wherein the stem cells are derived from a population of bone marrow cells.

3. The method of claim 2 wherein the stem cells are Lin− CD34+DR−.

4. The method of claim 1 wherein the stromal cells are human stromal cells.

5. The method of claim 1 wherein the stromal cell population is supported on a microporous membrane.

6. The method of claim 5 wherein the stromal cell population and the stem cell population are cultured on separable cell culture substrata.

7. The method of claim 6 wherein the stem cell population is supported by a microporous membrane, which membrane separates the stromal cell population from the stem cell population.

8. The method of claim 6 wherein the stromal population is adhered to the bottom of a plastic cell culture well.

9. The method of claim 1 wherein the stem cell population and the stromal cell population are separated by about 0.25-2 mm.

10. The method of claims 1 or 8 wherein the liquid stromal cell growth medium is 25-100% exchanged at intervals of about 8 hrs-14 days.

11. The method of claim 8 wherein the liquid stromal cell growth medium is continuously circulated through a chamber comprising said stromal cells.

12. The method of claim 4 wherein the populations are allogeneic.

13. The method of claim 4 wherein the populations are autologous.

* * * * *

UNITED STATES PATENT AND TRADEMARK OFFICE
CERTIFICATE OF CORRECTION

PATENT NO. : 5,436,151

DATED : Jul. 25, 1995

INVENTOR(S) : McGlave et al.

It is certified that error appears in the above-indentified patent and that said Letters Patent is hereby corrected as shown below:

Column 13, line 41, insert --†-- between "41" and "*".

Column 13, line 41, insert --†-- between "37" and "*".

Column 13, line 42, insert --†-- between "18" and "*".

Column 13, line 45, insert --:-- between "*" and "p".

Column 13, line 46, insert --†-- before ":p".

Column 13, line 46, delete "0.1" and insert --0.01--.

Column 15, line 9, insert --†-- after "89".

Column 15, line 14, insert --†-- before ":p".

Column 16, line 36, delete "medium" and insert --media--.

Column 16, line 39, delete "medium" and insert --media--.

Signed and Sealed this

Seventh Day of November, 1995

Attest:

Attesting Officer

BRUCE LEHMAN

Commissioner of Patents and Trademarks